US012778550B2

(12) United States Patent
Hu et al.

(10) Patent No.: US 12,778,550 B2
(45) Date of Patent: Nov. 3, 2026

(54) ROPE FIXATION DEVICE, ROPE TRANSMISSION DEVICE, AND ULTRASOUND PROBE

(71) Applicant: WUHAN UNITED IMAGING HEALTHCARE CO., LTD., Wuhan (CN)

(72) Inventors: Hao Hu, Wuhan (CN); Xiao-Yang Dong, Wuhan (CN); Kang Si, Shanghai (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 282 days.

(21) Appl. No.: 18/510,698

(22) Filed: Nov. 16, 2023

(65) Prior Publication Data

US 2024/0164753 A1 May 23, 2024

(30) Foreign Application Priority Data

Nov. 18, 2022 (CN) ......................... 202211444474.6

(51) Int. Cl.
*A61B 8/00* (2006.01)
*A61B 8/12* (2006.01)

(52) U.S. Cl.
CPC .............. *A61B 8/4461* (2013.01); *A61B 8/12* (2013.01)

(58) Field of Classification Search
CPC ..... B66B 11/08; B66B 11/06; B66B 11/0075; B66D 1/34; A61B 8/4466; A61B 8/4461; A61B 8/12

(Continued)

(56) References Cited

U.S. PATENT DOCUMENTS 9,482,312 B2 * 11/2016 Wingett ................ B64C 13/507
10,806,430 B2 * 10/2020 Tang .................... A61B 8/4444

(Continued)

FOREIGN PATENT DOCUMENTS

CN 201225382 Y * 4/2009
CN 104224228 A 12/2014

(Continued)

OTHER PUBLICATIONS

Chinese Office Action (Application No. 2022114444746 , dated Nov. 20, 2025, 6 pages.

(Continued)

*Primary Examiner* — T. Scott Fix

(57) ABSTRACT

The present application relates to a rope fixation device, a rope transmission device, and an ultrasound probe. The rope fixation device includes a drive shaft, a rope, and a fixing member. The drive shaft is provided with a rope through-hole and a fixing hole. The fixing hole is in communication with the rope through-hole. The rope through-hole penetrates through the drive shaft. Two opposite ends of the rope through-hole are both located on the side wall of the drive shaft. The rope extends through the rope through-hole, and two ends of the rope respectively protrude out from the two opposite ends of the rope through-hole. The fixing member is inserted into the fixing hole. One end of the fixing member adjacent to the rope through-hole includes an end surface. At least part of the end surface abuts against the rope, thereby fixing the rope in the rope through-hole.

17 Claims, 7 Drawing Sheets

(58) Field of Classification Search
USPC ........................... 600/444, 445, 446; 74/89.2
See application file for complete search history.

(56) References Cited

U.S. PATENT DOCUMENTS

| | | | |
|---|---|---|---|
| 2008/0161695 | A1 | 7/2008 | Kim et al. |
| 2015/0159739 | A1 | 6/2015 | Wingett et al. |
| 2016/0238113 | A1 | 8/2016 | Kiesel et al. |

FOREIGN PATENT DOCUMENTS

| | | | |
|---|---|---|---|
| CN | 104235296 | A | 12/2014 |
| CN | 219101980 | U | 5/2023 |
| DE | 102011078080 | A1 | 12/2012 |
| JP | 1997109627 | A | 4/1997 |
| KR | 1020170110961 | A | 10/2017 |
| KR | 20180069161 | A | 6/2018 |
| KR | 101965300 | B1 | 4/2019 |
| KR | 101965302 | B1 | 8/2019 |
| WO | 2019241833 | A1 | 12/2019 |

OTHER PUBLICATIONS

Tian Can et al., "Automatic detection method of tissue injuries caused by HIFU based on ultrasonic image processing: An experimental study", China J Med Imaging Technology, vol. 34, No. 10, Oct. 2, 2001, (6 pages).
Notice of Allowance of CN 202211444474.6.

* cited by examiner

ROPE FIXATION DEVICE, ROPE TRANSMISSION DEVICE, AND ULTRASOUND PROBE

CROSS-REFERENCE TO RELATED APPLICATIONS

The present application claims priority to Chinese patent application No. 202211444474.6, filed on Nov. 18, 2022, the content of which is hereby incorporated by reference in its entirety.

TECHNICAL FIELD

The present application relates to the technical field of medical devices, in particular to a rope fixation device, a rope transmission device, and an ultrasound probe.

BACKGROUND

An ultrasonic diagnostic apparatus is commonly employed for visualizing and diagnosing various aspects of a subject's body. It serves diverse purposes, including the detection of foreign substances within organs, the measurement of lesion severity, and the observation of conditions such as tumors or fetal development. To accomplish these tasks, ultrasonic diagnostic apparatuses typically utilize various ultrasound probes to gather detailed information about the subject's body. The ultrasound probe with three-dimensional (3D) imaging functions is called a 3D ultrasound probe, typically including a stepper motor as the driving power source and a transducer for emitting ultrasonic waves to an inspection portion and receiving reflected ultrasonic waves therefrom. The stepper motor can be controlled to drive a transmission device, so as to drive the transducer to rotate within a certain angle range in order to achieve 3D ultrasonic imaging.

The 3D ultrasound probe can be divided into two categories: the surface 3D ultrasound probe and the intracavitary 3D ultrasound probe. The intracavitary 3D ultrasound probe commonly adopts a rope transmission device to transmit the driving force. Specifically, the rope transmission device includes a driven shaft, a pulley, a drive shaft, and a rope. The transducer of the 3D ultrasound probe is arranged on the driven shaft, thereby moving with the driven shaft. The two opposite ends of the rope are fixed to the drive shaft, and the rope is connected to the driven shaft via the pulley. The rotation force can be transmitted from the drive shaft to the driven shaft through the rope, and the driven shaft can be driven to rotate with the drive shaft.

SUMMARY

In view of the above, the present application provides a rope fixation device, a rope transmission device, and an ultrasound probe.

In a first aspect, the present application provides a rope fixation device for an ultrasound probe. The rope fixation device includes a drive shaft, a rope, and a fixing member. The drive shaft is provided with a rope through-hole and a fixing hole. The fixing hole is in communication with the rope through-hole. The rope through-hole penetrates through the drive shaft. Two opposite ends of the rope through-hole are both located on the side wall of the drive shaft. The body of the rope is located in the rope through-hole, and two ends of the rope respectively protrude out from the two opposite ends of the rope through-hole. The fixing member is inserted into the fixing hole. One end of the fixing member adjacent to the rope through-hole includes an end surface. At least part of the end surface abuts against the rope, thereby fixing the rope in the rope through-hole.

In an embodiment, the rope through-hole is a straight line-shaped hole.

In an embodiment, the fixing hole includes a first fixing hole and a second fixing hole, spaced apart from each other on the drive shaft.

In an embodiment, the center line of the rope through-hole intersects the axis of the drive shaft.

In an embodiment, the center line of the rope through-hole is not perpendicular to the axis of the drive shaft.

In an embodiment, the first fixing hole and the second fixing hole are disposed on two sides of the rope through-hole, and the center lines of the first fixing hole and the second fixing hole are both perpendicular to the axis of the drive shaft. The fixing member includes a first fixing member and a second fixing member, respectively inserted into the first fixing hole and the second fixing hole. The end surface of the first fixing member and the end surface of the second fixing member respectively abut against the rope.

In an embodiment, the center lines of the first fixing hole and the second fixing hole are spaced from each other by a first distance. A ratio of the first distance to the length of the rope through-hole is in a range from 0.4 to 0.6.

In an embodiment, the first fixing hole and the second fixing hole are centrally symmetric with respect to the center of the rope through-hole.

In an embodiment, the first fixing hole and the second fixing hole are disposed on two sides of the rope through-hole, and the center lines of the first fixing hole and the second fixing hole are both perpendicular to the center line of the rope through-hole. The end surface of the first fixing member and the end surface of the second fixing member respectively abut against the rope.

In an embodiment, the center lines of the first fixing hole and the second fixing hole are spaced from each other by a second distance. A ratio of the second distance to the length of the rope through-hole is in a range from 0.3 to 0.7.

In an embodiment, the first fixing hole and the second fixing hole are centrally symmetric with respect to the center of the rope through-hole.

In an embodiment, the center line of the rope through-hole is perpendicular to the axis of the drive shaft.

In an embodiment, the center lines of the first fixing hole and the second fixing hole are both perpendicular to the center line of the rope through-hole, and the center lines of the first fixing hole and the second fixing hole are parallel to the axis of the drive shaft. The end surface of the first fixing member and the end surface of the second fixing member respectively abut against the rope.

In an embodiment, the center lines of the first fixing hole and the second fixing hole are both perpendicular to the center line of the rope through-hole. The center line of the first fixing hole is perpendicular to the axis of the drive shaft, and the center line of the second fixing hole is parallel to the axis of the drive shaft. The end surface of the first fixing member and the end surface of the second fixing member respectively abut against the rope.

In an embodiment, at least one of the first fixing hole and the second fixing hole is located on the side wall of the drive shaft.

In an embodiment, the fixing hole is a blind hole, extending in the drive shaft and terminating in the rope through-hole, such that the end surface of the fixing member presses the rope against the inner wall of the rope through-hole.

In an embodiment, the fixing hole includes a first hole section and a second hole section connected to and in communication with the first hole section. One end of the first hole section is connected to and in communication with the rope through-hole, and the other end of the first hole section is connected to and in communication with the second hole section. The diameter of the first hole section is larger than the diameter of the second hole section.

The fixing member includes a first segment and a second segment that are connected to each other. The first segment is located in the first hole section, and the second segment is located in the second hole section. The outer diameter of the first segment is larger than the outer diameter of the second segment. The first segment is an elastic member.

In a second aspect, the present application provides a rope transmission device for an ultrasound probe. The rope transmission device includes a driven shaft and the rope fixation device described above in the first aspect. The rope of the rope fixation device is connected to the driven shaft.

In a third aspect, the present application provides an ultrasound probe. The ultrasound probe includes the rope transmission device described above in the second aspect.

In the above-described embodiments of the rope fixation device, rope transmission device, and ultrasound probe, at least part of the end surface of the fixing member abuts against the rope, so that a force can be exerted onto the rope through the end surface of the fixing member rather than through a lateral surface of the fixing member. As such, the fixing member can exert a greater force onto the rope, thereby improving the effectiveness of securing the rope. In addition, the rope is threaded from one end of the rope through-hole to the other end of the rope through-hole. Compared with respectively inserting the two opposite ends of the rope into the two opposite ends of the rope through-hole, the threading of the rope in the present application not only makes the assembly of the rope more convenient, but also prevents one or both ends of the rope from detaching, thereby improving the reliability of rope fastening.

BRIEF DESCRIPTION OF THE DRAWINGS

In order to illustrate the embodiments of the present application more clearly, the drawings used in the embodiments will be described briefly. Apparently, the following described drawings are merely for the embodiments of the present application, and other drawings can be derived by those of ordinary skill in the art without any creative effort.

REFERENCE SIGNS

Figure 1:
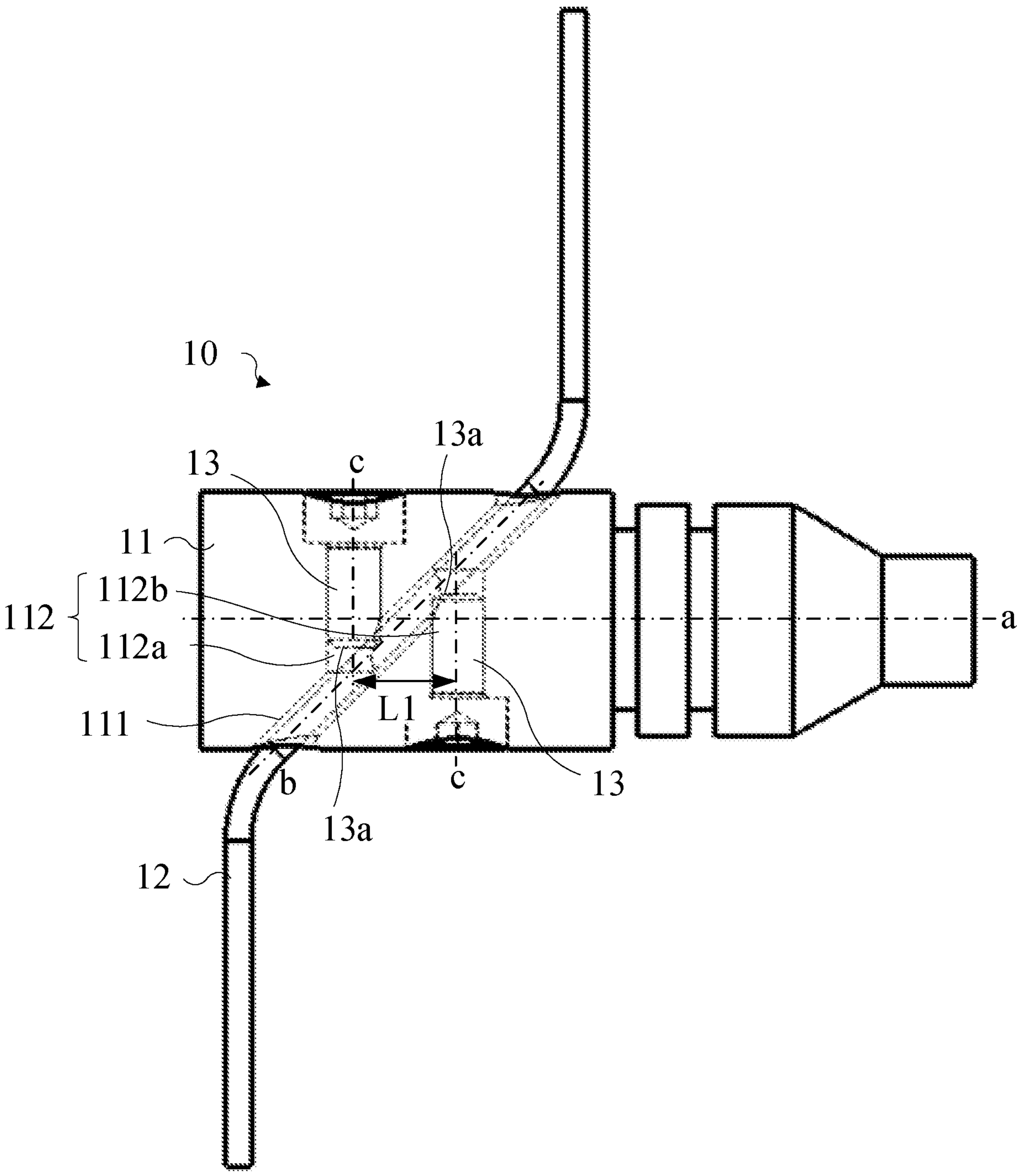
FIG. 1 is a schematic structural view of an embodiment of a rope fixation device provided by the present application.

1, rope transmission device; 10, rope fixation device; 11, drive shaft; 111, rope through-hole; 112, fixing hole; 1121, first hole section; 1122, second hole section; 12, rope; 13, fixing member; **13*a*, end surface; 131, first segment; 132, second segment; 20, driven shaft; 30**, transducer.

DETAILED DESCRIPTION

To make the objectives, features, and advantages of the present application more understandable, detailed explanations of specific embodiments are provided below, along with accompanying drawings. Many specific details are disclosed in the following description to facilitate a comprehensive understanding of the present application. However, it should be noted that the present application can be implemented in various ways different from those described herein, and those skilled in the art may make similar improvements without departing from the scope of the present application. Therefore, the present application is not limited to the specific embodiments disclosed below.

In the description of the present application, it should be understood that the terms "central", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial", "circumferential", etc. indicate the orientations or positional relationships on the basis of the drawings. These terms are only for describing the present application and simplifying the description, rather than indicating or implying that the related devices or elements must have the specific orientations, or be constructed or operated in the specific orientations, and therefore cannot be understood as limitations of the present application.

In addition, the terms "first" and "second" are used merely as labels to distinguish one element having a certain name from another element having the same name, and cannot be understood as indicating or implying any priority, precedence, or order of one element over another, or indicating the quantity of the element. Therefore, the element modified by "first" or "second" may explicitly or implicitly includes at least one of the elements. In the description of the present application, "a plurality of" means at least two, such as two, three, etc., unless otherwise specifically defined.

In the present application, unless otherwise clearly specified and defined, the terms "installed", "connected", "coupled", "fixed" and the like should be interpreted broadly. For example, an element, when being referred to as being "installed", "connected", "coupled", "fixed" to another element, unless otherwise specifically defined, may be fixedly connected, detachably connected, or integrated to the other element, may be mechanically connected or electrically connected to the other element, and may be directly connected to the other element or connected to the other element via an intermediate element. For those of ordinary skill in the art, the specific meaning of the above-mentioned terms in the present application can be understood according to specific circumstances.

In the present application, unless otherwise specifically defined, an element, when being referred to as being located "on" or "under" another element, may be in direct contact with the other element or contact the other element via an intermediate element. Moreover, the element, when being referred to as being located "on", "above", "over" another element, may be located right above or obliquely above the other element, or merely located at a horizontal level higher than the other element; the element, when being referred to as being located "under", "below", "beneath" another element, may be located right below or obliquely below the other element, or merely located at a horizontal level lower than the other element.

It should be noted that an element, when being referred to as being "fixed" or "mounted" to another element, may be directly fixed or mounted to the other element or via an intermediate element. Such terms as "vertical", "horizontal", "up", "down", "left", "right" and the like used herein are for illustrative purposes only and are not meant to be the only ways for implementing the present application.

The terminology used herein is for the purpose of describing particular embodiments only and is not intended to limit the present application. As used herein, the singular forms with "a", "an", "the", or "said" are intended to include the plural forms as well, unless the context clearly indicates otherwise. It should also be understood that the terms "consists of" and "comprising", when used in the present application, identify the presence of the stated features, integers, steps, operations, elements and/or parts, but do not exclude presence or addition of one or more other features, integers, steps, operations, elements, parts and/or groups. As used herein, the term "and/or" means that any one of the listed items can be employed by itself or any combination of two or more of the listed items can be employed.

In the related art, two ends of a rope may be inserted into radial holes on a drive shaft, and a fixing member may be inserted into an axial hole on the drive shaft, such that the lateral surface of the fixing member and the inner wall of the axial hole cooperatively squeeze the two ends of the rope, thereby fixing the rope. However, on the one hand, this structure try to simultaneously secure the two ends of the rope, which introduces the risk of detachment on either or both ends of the rope. On the other hand, the fixation reliability provided by this structure is inadequate, and the rope is susceptible to loosening and detachment.

In view of the above, embodiments of the present application provide a rope fixation device, a rope transmission device, and an ultrasound probe, which not only improve fixation effectiveness for the rope, but also prevent one or both ends of the rope from detaching, thereby improving the reliability of the rope fastening.

In a first aspect, referring to FIGS. 1 to 5, an embodiment of the present application provides a rope fixation device 10 for an ultrasound probe. The rope fixation device 10 includes a drive shaft 11, a rope 12, and a fixing member 13. The drive shaft 11 is provided with a rope through-hole 111 and a fixing hole 112. The fixing hole 112 is in communication with the rope through-hole 111. The rope through-hole 111 penetrates through the drive shaft 11. Two opposite ends of the rope through-hole 111 are both located on the side wall of the drive shaft 11.

Specifically, the rope 12 is inserted into the rope through-hole 111, wherein one end of the rope 12 is inserted from one end of the rope through-hole 111 and protrudes out from the other end of the rope through-hole 111. The rope 12 extends through the rope through-hole 111, the body of the rope 12 is located in the rope through-hole 111, and the two ends of the rope 12 respectively protrude out from the two opposite ends of the rope through-hole 111. Compared with disposing the two ends of the rope 12 in the rope through-hole 111, it is an integrated rope body that extends through the rope through-hole 111 in the present embodiment, eliminating the risk of detachment of one or both ends of the rope 12 from the rope through-hole 111. In addition, during threading the rope 12, it only needs to pass either end of the rope 12 through the rope through-hole 111, and there is no need to insert both ends, thus making the assembly of the rope 12 with the drive shaft 11 more convenient. The rope 12 can be prevented from detachment from the rope through-hole 111, thereby improving the fastening reliability of the rope 12.

Specifically, the fixing member 13 is inserted into the fixing hole 112. One end of the fixing member 13 adjacent to the rope through-hole 111 includes an end surface 13*a*. At least part of the end surface 13*a* is in contact with and abuts against the rope 12, thereby fixing the rope 12 in the rope through-hole 111. In some embodiments, the fixing hole 112 is a blind hole, extending in the drive shaft 11 and terminating in the rope through-hole 111, such that the end surface 13*a* presses the rope 12 against the inner wall of the rope through-hole 111. The diameter of the rope through-hole 111 is in correspondence with the diameter of the rope 12, in order to allow the rope 12 to just able to extend through the rope through-hole 111, leaving no room for the rope 12 curved in the rope through-hole 111. The fixing hole 112 can be disposed on the end surface and/or the side wall of the drive shaft 11. Disposing the fixing hole 112 and the corresponding fixing member 13 on the side wall of the drive shaft 11 is in favor of decreasing the diameter of the drive shaft 11, and thus in favor of minimizing the size of the ultrasound probe. The fixing member 13 is configured to fix the rope 12. The fixing member 13 may be a pin, a screw, a bolt, etc. When the fixing member 13 is a pin, the fixing hole 112 can be a pin hole. When the fixing member 13 is a screw or a bolt, the fixing hole 112 can be a threaded hole, and the pressing force applied to the rope 12 can be controlled by adjusting the screw-in depth of the screw or the bolt, making sure that the rope 12 has sufficient compression to ensure the fixation reliability. In some embodiments, the fixing member 13 can be made of wax, glue, etc. that meet the strength requirements. Specifically, a liquid material can be injected into the fixing hole 112, and solidified to in-situ form the fixing member 13 in the fixing hole 112, thereby fixing the rope 12 in the rope through-hole 111.

The fixing hole 112 can be a countersunk hole to allow the head of the screw or bolt to be nested in the countersunk hole, thereby making the side wall of the drive shaft 11 smooth. The opposite ends of the rope through-hole 111 can be provided with rounded corners to facilitate threading the rope 12 through the rope through-hole 111.

In some embodiments, the end surface 13*a* of the fixing member 13 can refer to the surface of the fixing member 13 furthest away from the center of the fixing member 13 along the axial direction thereof, and the lateral surface of the fixing member 13 can refer to the surface of the fixing member 13 furthest away from the center of the fixing member 13 along the radial direction thereof. It should be understood that when the fixing member 13 is "inserted" or "screwed" into the fixing hole 112, the fixing member 13 advances toward the rope through-hole 111 along the axial direction of the fixing member 13. The fixing member 13 can provide a pressing force along the axial direction of the fixing member 13. Since at least part of the end surface 13*a* of the fixing member 13 abuts against the rope 12, the pressing force can be directly applied to the rope 12 through the at least part of the end surface 13*a*. Compared with applying force to the rope 12 through the lateral surface of the fixing member in the related art, a greater force can be applied to the rope 12 by the fixing member 13 in the present embodiment, thereby improving the fixing effect on the rope 12.

In addition, in the related art, the lateral surface of the screw or bolt as the fixing member may rub and cause damage to the rope 12. Even to combine a pin with a bolt to diminish the damage, the combination is complicated to make and has poor replaceability. In contrast, as it is the end surface 13*a* that exerts the force to the rope 12, the fixing member 13 can be a standard part, such as a standard screw, bolt, or pin, thereby having good interchangeability.

In some embodiments, as shown in FIGS. 1 to 5, the rope through-hole 111 is a straight line-shaped hole. Specifically, the center line b of the rope through-hole 111 can be a straight line.

On the condition that the rope through-hole 111 is a straight line-shaped hole, the rope through-hole 111 can be easily formed in the drive shaft 11, i.e., the processing difficulty of the rope through-hole 111 can be reduced; in addition, the rope 12 can be easily threaded through the rope through-hole 111, i.e., the assembly difficulty of the rope 12 can also be reduced.

In some embodiments, the number of the fixing holes 112 is two, i.e., there are a first fixing hole 112*a* and a second fixing hole 112*b*, and the two fixing holes 112 are spaced apart from each other on the drive shaft 11. Correspondingly, the number of fixing members 13 is also two, i.e., there are a first fixing member and a second fixing member, and the two fixing members 13 are disposed in the two fixing holes 112 in one-to-one correspondence.

By including the two fixing holes 112 and the two fixing members 13, the fixing stability of the rope 12 in the drive shaft 11 can be further improved. The two fixing members 13 in the two fixing holes 112 can form a "double insurance", so that even if one fixing member 13 becomes loose, the rope 12 can still be secured by the other fixing member 13 and not become loose or fall off.

In some embodiments, as shown in FIGS. 1 to 4, the rope through-hole 111 intersects the axis a of the drive shaft 11, and the two opposite ends of the rope through-hole 111 are respectively located on the side wall of the drive shaft 11 and on two opposite sides of the drive shaft 11 in the radial direction. In some embodiments, the center line b of the rope through-hole 111 intersects with the axis a of the drive shaft 11. The axis a of the drive shaft 11 can be a rotation axis of the drive shaft 11.

Taking the orientation in FIG. 1 as an example, the center line b of the rope through-hole 111 intersects with the axis a of the drive shaft 11, so that the length of the rope through-hole 111 in the "upper half" of the drive shaft 11 above the axis a is equal to the length of the rope through-hole 111 in the "lower half" of the drive shaft 11 below the axis a, thus making the weights of the "upper half" and the "lower half" of the drive shaft 11 approximately equal. As a result, the center of gravity of the drive shaft 11 substantially coincides with its center of geometry, avoiding damage to the drive motor connected to the drive shaft 11 due to any offset in the center of gravity, which extends the service life of the drive motor. In addition, during rotation of the drive shaft 11, the force on the drive shaft 11 is relatively balanced, which improves the stability of the rotation.

In some embodiments, as shown in FIG. 1, the center line b of the rope through-hole 111 is not perpendicular to the axis a of the drive shaft 11. Taking the orientation in FIG. 1 as an example, this arrangement can make the two parts of the rope 12 located outside the rope through-hole 111 staggered from each other in both the axial direction and the radial direction of the drive shaft 11, thereby avoiding the two parts of the rope 12 from interference with each other when the drive shaft 11 rotates.

In some embodiments, as shown in FIG. 1, the two fixing holes 112 are disposed on two sides of the rope through-hole 111, and the center lines c of the two fixing holes 112 are perpendicular to the axis a of the drive shaft 11. That is, the center lines c of the two fixing holes 112 are parallel to the radial direction of the drive shaft 11. A part of the end surface 13*a* of each of the fixing members 13 is in contact with and abuts against the rope 12.

Taking the orientation in FIG. 1 as an example, in the above arrangement, the two fixing members 13 are respectively disposed in the "upper half" and "lower half" of the drive shaft 11, thus making the weights of the "upper half" and the "lower half" of the drive shaft 11 approximately equal. As a result, the center of gravity of the drive shaft 11 substantially coincides with its center of geometry, avoiding damage to the drive motor connected to the drive shaft 11 due to any offset in the center of gravity, which extends the service life of the drive motor. In addition, during rotation of the drive shaft 11, the force on the drive shaft 11 is relatively balanced, which improves the stability of the rotation. Moreover, since the fixing holes 112 are radial holes, the difficulty of drilling the fixing holes 112 can be reduced.

In some embodiments, as shown in FIG. 1, there is a first distance L1 between the center lines c of the two fixing holes 112. The ratio of the first distance L1 to the length of the rope through-hole 111 is in a range from 0.4 to 0.6. The length of the rope through-hole 111 refers to the distance between the two opposite ends of the rope through-hole 111.

It should be understood that the intersection points of the two fixing holes 112 and the rope through-hole 111 is the points where the two fixing members 13 exert two fixing forces on the rope 12. The above ratio can make the distance between the two points of force application moderate, that is, neither too close nor too far apart, so that the rope 12 can be more stably fixed in the drive shaft 11.

Specifically, the two fixing holes 112 are centrally symmetric with respect to the center of the rope through-hole 111. The distance between the first fixing hole 112*a* and one end of the rope through-hole 111 most adjacent to the first fixing hole 112*a* is equal to the distance between the second fixing hole 112*b* and the other end of the rope through-hole 111 most adjacent to the second fixing hole 112*b*.

The above arrangement can make the two points of force application evenly distributed in the rope through-hole 111, so that the fixing force borne by the rope 12 is relatively uniform, and that the rope 12 can be more stably fixed in the drive shaft 11.

Figure 2:
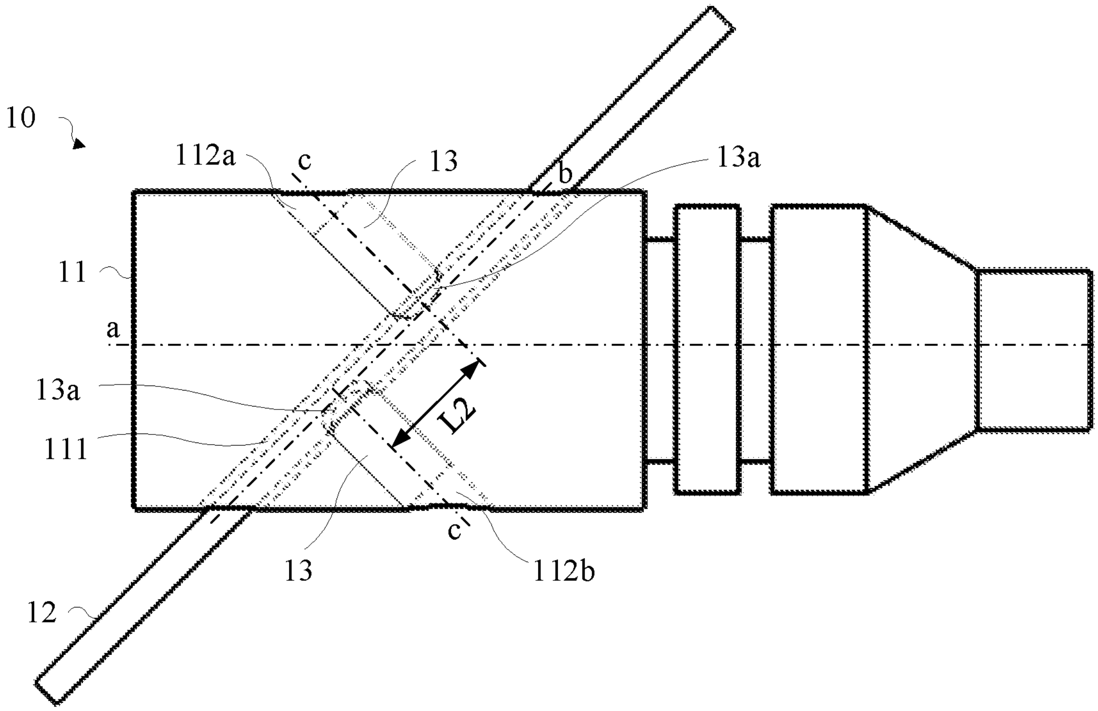
FIG. 2 is a schematic structural view of another embodiment of the rope fixation device provided by the present application.

In some embodiments, referring to FIG. 2, the two fixing holes 112 are disposed on two sides of the rope through-hole 111, and the center lines c of the two fixing holes 112 are perpendicular to the center line b of the rope through-hole 111. The entire end surface 13*a* of each fixing member 13 is in contact with and abuts against the rope 12.

In this way, on the one hand, the entire end surface 13*a* of each fixing member 13 can be in contact with and abuts against the rope 12, so that the pressing force applied by the fixing members 13 on the rope 12 is increased, improving the fixing effect on the rope 12. On the other hand, when the drive shaft 11 rotates, centrifugal force along the radial direction will be generated. Since the center lines c of the fixing holes 112 are not parallel to the radial direction of the drive shaft 11, when the fixing members 13 are about to loosen due to centrifugal force, the fixing members 13 will be subjected to a force parallel to the radial direction of the drive shaft 11, countering the centrifugal force, by the inner wall of the fixing holes 112, thereby maximizing the prevention of the fixing members 13 from detaching from the fixing holes 112. This enhances the stability of the fixing member 13.

In some embodiments, as shown in FIG. 2, there is a second distance L2 between the center lines c of the two fixing holes 112. The ratio of the second distance L2 to the length of the rope through-hole 111 is in a range from 0.3 to 0.7. The length of the rope through-hole 111 refers to the distance between the two opposite ends of the rope through-hole 111.

It can be understood that the intersection points of the two fixing hole 112 and the rope through-hole 111 is the points where the fixing members 13 exert two fixing forces on the rope 12. The above ratio can make the distance between the two points of force application moderate, that is, neither too close nor too far apart, so that the rope 12 can be more stably fixed in the drive shaft 11.

Specifically, the two fixing holes 112 are centrally symmetric with respect to the center of the rope through-hole 111. The distance between the first fixing hole 112*a* and one end of the rope through-hole 111 most adjacent to the first fixing hole 112*a* is equal to the distance between the second fixing hole 112*b* and the other end of the rope through-hole 111 most adjacent to the second fixing hole 112*b*.

The above arrangement can make the two points of force application evenly distributed in the rope through-hole 111, so that the fixing force borne by the rope 12 is relatively uniform, and that the rope 12 can be more stably fixed in the drive shaft 11.

Figure 3:
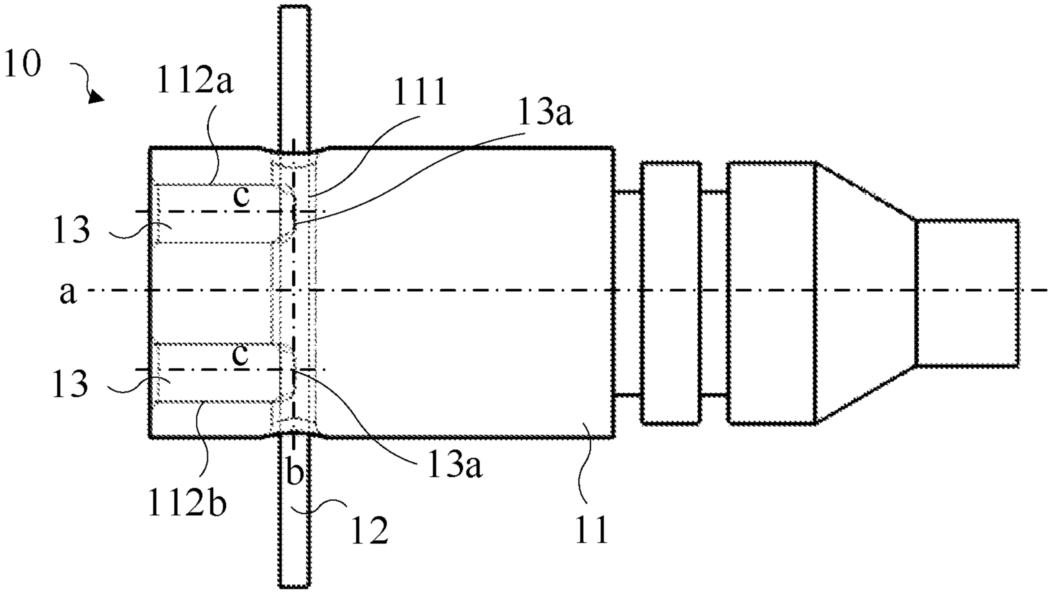
FIG. 3 is a schematic structural view of yet another embodiment of the rope fixation device provided by the present application.
Figure 4:
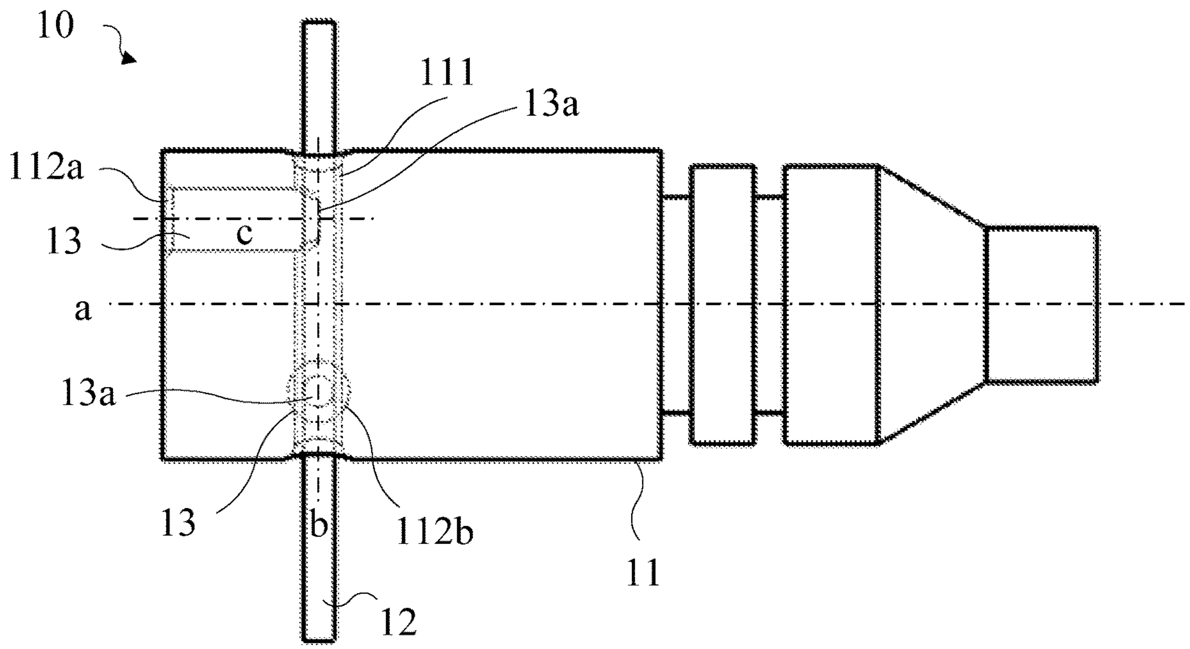
FIG. 4 is a schematic structural view of yet another embodiment of the rope fixation device provided by the present application.

In some embodiments, referring to FIGS. 3 and 4, the center line b of the rope through-hole 111 is perpendicular to the axis a of the drive shaft 11. In this way, the rope through-hole 111 is a radial hole, which can reduce the difficulty of drilling the rope through-hole 111.

In some embodiments, as shown in FIG. 3, the two fixing holes 112 are both located on the end surface of the drive shaft 11, the center lines c of the two fixing holes 112 are both perpendicular to the center line b of the rope through-hole 111, and the center lines c of the two fixing holes 112 are parallel to the axis a of the drive shaft 11. The entire end surface 13*a* of each fixing member 13 is in contact with and abuts against the rope 12.

In this way, on the one hand, the entire end surface 13*a* of each fixing member 13 can be in contact with and abut against the rope 12, so that the pressing force exerted by the fixing members 13 on the rope 12 is increased, improving the fixing effect on the rope 12. On the other hand, when the drive shaft 11 rotates, the fixing members 13 are not affected by the centrifugal force and thus remain stable.

In some embodiments, the two fixing holes 112 are symmetric with respect to the axis a of the drive shaft 11. In this way, the center of gravity of the drive shaft 11 substantially coincides with its center of geometry, avoiding damage to the drive motor connected to the drive shaft 11 due to any offset in the center of gravity, which extends the service life of the drive motor. In addition, during rotation of the drive shaft 11, the force on the drive shaft 11 is relatively balanced, which improves the stability of the rotation. In some embodiments, the distance between the two fixing members 13 can be moderate, that is, neither too close nor too far apart, so that the rope 12 can be more stably fixed in the drive shaft 11.

In some embodiments, as shown in FIG. 4, the center lines c of the two fixing holes 112 are both perpendicular to the center line b of the rope through-hole 111, wherein the center line c of the first fixing hole 112*b* is perpendicular to the axis a of the drive shaft 11, and the center line c of the second fixing hole 112*a* is parallel to the axis a of the drive shaft 11. The entire end surface 13*a* of each fixing member 13 is in contact with and abuts against the rope 12.

In this way, on the one hand, the entire end surface 13*a* of each fixing member 13 can be in contact with and abut against the rope 12, so that the pressing force exerted by the fixing members 13 on the rope 12 is increased, improving the fixing effect on the rope 12. On the other hand, the two fixing members 13 exert pressing forces on the rope 12 in different directions, so that the rope 12 can be subjected to the pressing forces in two different directions, and the rope 12 can be more stably fixed in the drive shaft 11.

Specifically, the first fixing hole 112*b* is disposed on the side wall of the drive shaft 11, and the center line c of the first fixing hole 112*b* is perpendicular to the axis a of the drive shaft 11; the second fixing hole 112*a* is disposed on the end surface of the drive shaft 11, and the center line c of the second fixing hole 112*a* is parallel to the axis a of the drive shaft 11.

In some embodiments, the distance between the center line c of each fixing hole 112 and the axis a of the drive shaft 11 is equal. In this way, the center of gravity of the drive shaft 11 substantially coincides with its center of geometry, avoiding damage to the drive motor connected to the drive shaft 11 due to any offset in the center of gravity, which extends the service life of the drive motor. In addition, during rotation of the drive shaft 11, the force on the drive shaft 11 is relatively balanced, which improves the stability of the rotation.

Figure 5:
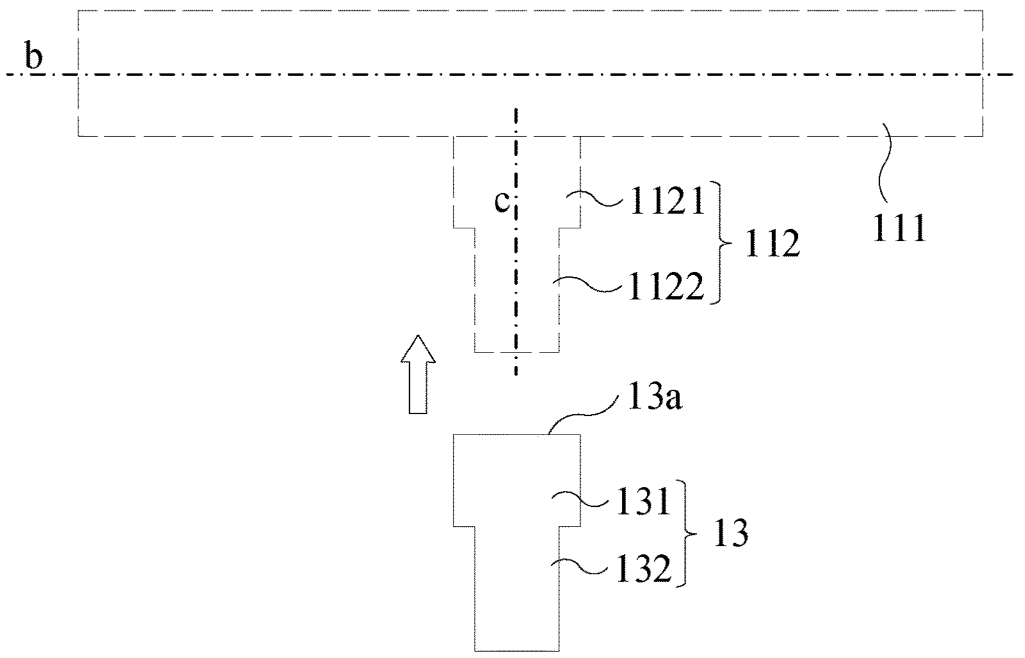
FIG. 5 is a schematic view showing an embodiment of assembling a fixing member into a fixing hole in communication with a rope through-hole, provided by the present application.

In some embodiments, referring to FIG. 5, the fixing hole 112 includes a first hole section 1121 and a second hole section 1122 connected to and in communication with the first hole section 1121. One end of the first hole section 1121 is connected to and in communication with the rope through-hole 111, and the other end of the first hole section 1121 is connected to and in communication with the second hole section 1122. The diameter of the first hole section 1121 is larger than the diameter of the second hole section 1122. The fixing member 13 includes a first segment 131 and a second segment 132 that are connected to each other. The first segment 131 is located in the first hole section 1121, and the second segment 132 is located in the second hole section 1122. The outer diameter of the first segment 131 is larger than the outer diameter of the second segment 132. The first segment 131 is an elastic structure, e.g., an elastic member.

By using an elastic member as the first segment 131, when the fixing member 13 is inserted into the fixing hole 112, the first segment 131 can be elastically deformed, making it easier to insert the fixing member 13 into the fixing hole 112.

In addition, the above arrangement can make the fixing member 13 not easy to detach from the fixing hole 112, which improves the stability of the fixing member 13. Moreover, the contact area between the end surface 13*a* of the fixing member 13 and the rope 12 can be increased, so that the rope 12 can be further compressed by the fixing member 13, and that the rope 12 can be more stably fixed in the drive shaft 11.

It can be understood that both the first segment 131 and the second segment 132 can be elastic members.

Figure 6:
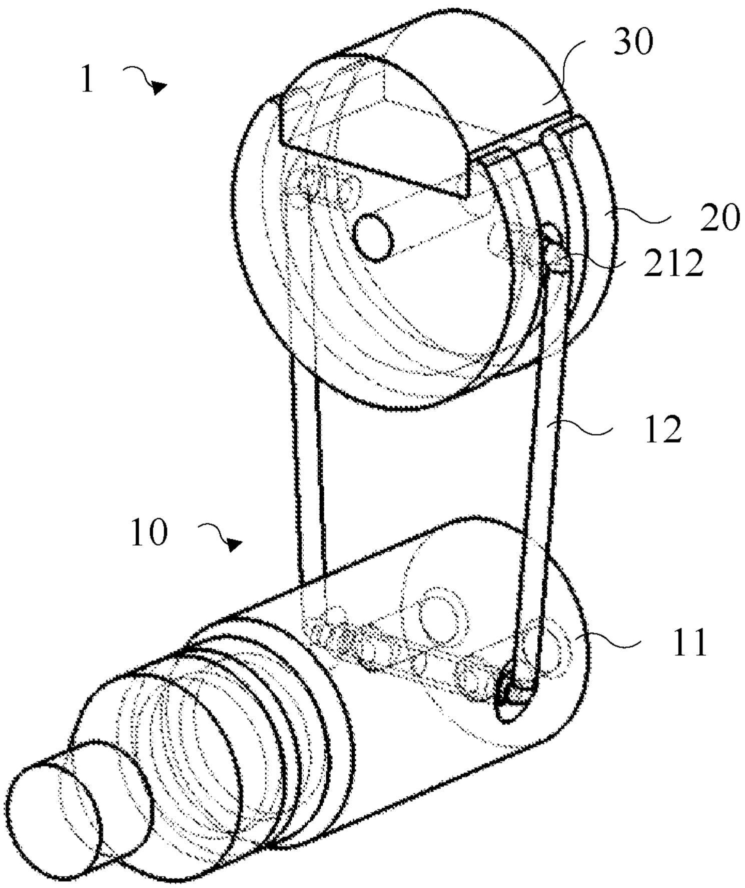
FIG. 6 is a schematic structural view of an embodiment of a rope transmission device provided by the present application.
Figure 7:
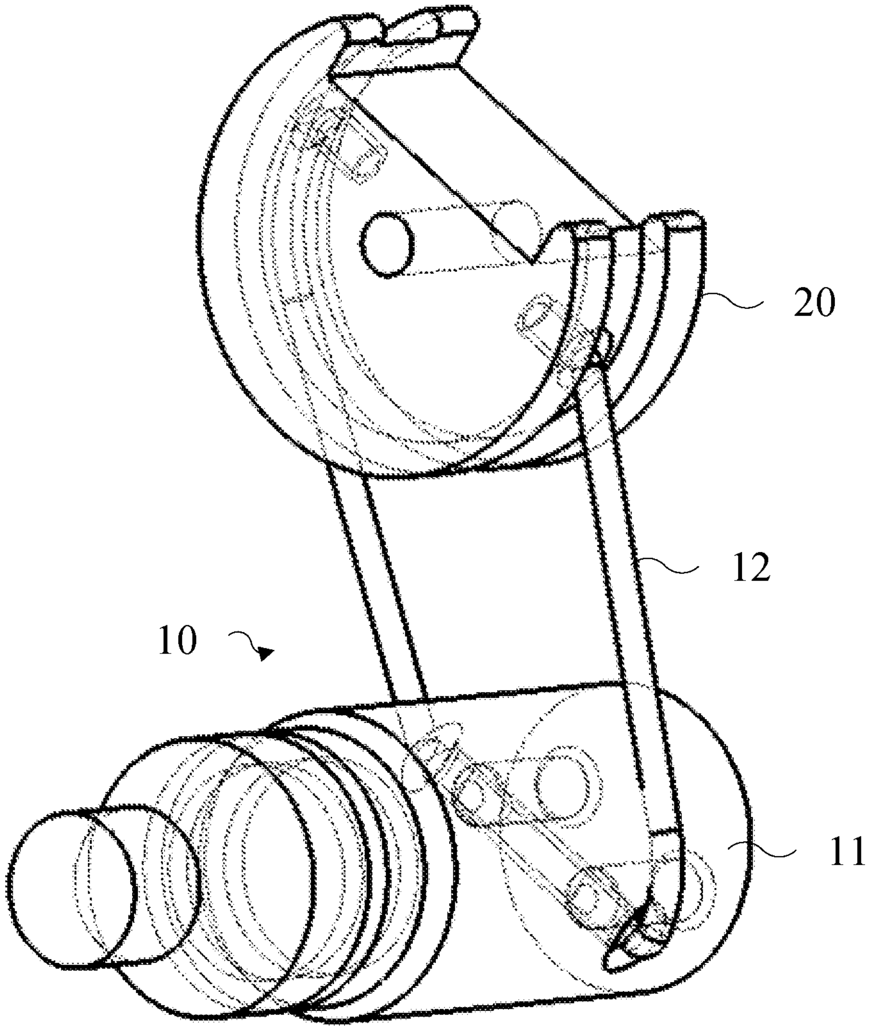
FIG. 7 is a schematic structural partial view of the rope transmission device of FIG. 6 from a first perspective.
Figure 8:
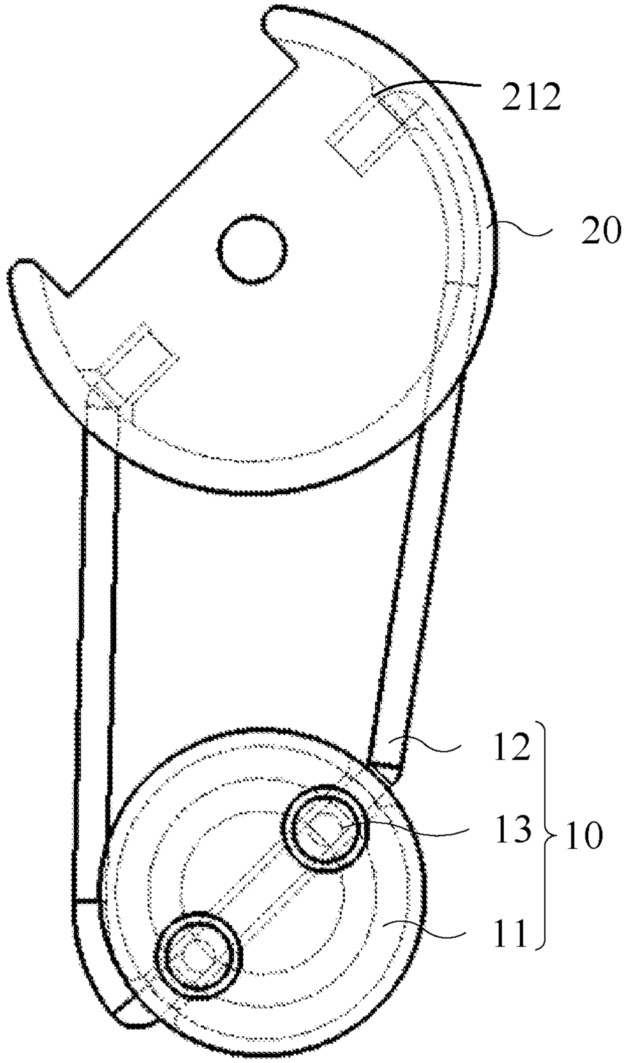
FIG. 8 is a schematic structural partial view of the rope transmission device of FIG. 6 from a second perspective.

In a second aspect, referring to FIGS. 6, 7 and 8, in conjunction with FIGS. 1 to 5, an embodiment of the present application provides a rope transmission device 1 for an ultrasound probe. The rope transmission device 1 includes a driven shaft 20 and the rope fixation device 10. The rope 12 of the rope fixation device 10 is connected to driven shaft 20.

Specifically, the two ends of the rope 12 are connected to the driven shaft 20. When the drive shaft 11 rotates, the driven shaft 20 is driven to rotate through the rope 12. In some embodiments, the two ends of the rope 12 are respectively fixed to the side wall of the driven shaft 20. Correspondingly, the side wall of the driven shaft 20 is provided with two rope-end holes 212, e.g., blind hoes, adapted to receive and fix the two ends of the rope 12 therein. The two rope-end holes 212 can be opposite to each other along the radial direction of the driven shaft 20. The two ends of the rope 12 are respectively inserted into the two rope-end holes 212. In some embodiments, a connection line from one rope-end hole 212 to the other rope-end hole 212 intersects the axis of rotation of the driven shaft 20.

In some embodiments, the connection line from one rope-end hole 212 to the other rope-end hole 212 is parallel to the center line b of the rope through-hole 111. In some embodiments, the two portions of the rope 12 between the drive shaft 11 and the driven shaft 20 are equal in length to each other.

In some embodiments, the two ends of the rope 12 are respectively fixed to the side wall of the driven shaft 20 by a fixing member, such as a pin, a screw, a block, etc. In some other embodiments, after inserting the two ends of the rope 12 into the rope-end holes 212, a liquid material, such as wax, glue, etc. that meets the strength requirements, can be injected into the rope-end holes 212, and solidified to in-situ form the fixing members in the rope-end holes 212, thereby fixing the two ends of the rope 12 in the rope-end holes 212.

In the rope transmission device 1, at least part of the end surface 13*a* of the fixing member 13 abuts against the rope 12, so that a force can be exerted onto the rope 12 through the end surface 13*a* of the fixing member 13 rather than through a lateral surface of the fixing member 13. As such, the fixing member 13 can exert a greater force onto the rope 12, thereby improving the effectiveness of securing the rope 12. In addition, the rope 12 is threaded from one end of the rope through-hole 111 to the other end of the rope through-hole 111. Compared with respectively inserting the two opposite ends of the rope 12 into the rope through-hole, it is an integrated rope body that extends through the rope through-hole 111 in the present embodiment, eliminating the risk of detachment of one or both ends of the rope 12 from the rope through-hole 111. In addition, the assembly of the rope 12 with the drive shaft 11 is more convenient.

In a third aspect, referring to FIGS. 6, 7 and 8, and in combination with FIGS. 1 to 5, the present application provides an ultrasound probe, which includes the rope transmission device 1.

Specifically, the ultrasound probe further includes a transducer 30 and a motor (not shown). The motor is connected to the drive shaft 11, and the motor is configured to drive the drive shaft 11 to rotate.

In the ultrasound probe, at least part of the end surface 13*a* of the fixing member 13 abuts against the rope 12, so that a force can be exerted onto the rope 12 through the end surface 13*a* of the fixing member 13 rather than through a lateral surface of the fixing member 13. As such, the fixing member 13 can exert a greater force onto the rope 12, thereby improving the effectiveness of securing the rope 12. In addition, the rope 12 is threaded from one end of the rope through-hole 111 to the other end of the rope through-hole 111. Compared with respectively inserting the two opposite ends of the rope 12 into the rope through-hole, it is an integrated rope body that extends through the rope through-hole 111 in the present embodiment, eliminating the risk of detachment of one or both ends of the rope 12 from the rope through-hole 111. In addition, the assembly of the rope 12 with the drive shaft 11 is more convenient.

In the description of the present specification, the terms such as "some embodiments," "other embodiments," "preferred embodiments," etc., indicate that the specific features, structures, materials, or characteristics described in combination with that embodiment or example are included in at least one embodiment or example of the present application. In the present specification, these terms does not necessarily refer to the same embodiment or example.

The technical features of the above-mentioned embodiments can be combined arbitrarily. In order to make the description concise, not all possible combinations of the technical features are described in the embodiments. However, as long as there is no contradiction in the combination of these technical features, the combinations should be considered as in the scope of the present application.

The above-described embodiments are only several implementations of the present application, and the descriptions are relatively specific and detailed, but they should not be construed as limiting the scope of the present application. It should be understood by those of ordinary skill in the art that various modifications and improvements can be made without departing from the concept of the present application, and all fall within the protection scope of the present application. Therefore, the patent protection of the present application shall be defined by the appended claims.

What is claimed is:

1. A rope fixation device for ultrasound probe, comprising:

a drive shaft, provided with a rope through-hole and a fixing hole, the fixing hole being in communication with the rope through-hole, the rope through-hole penetrating through the drive shaft, and two opposite ends of the rope through-hole being located on a side wall of the drive shaft;

a rope, whose body being located in the rope through-hole, and two ends of the rope respectively protruding out from the two opposite ends of the rope through-hole; and a fixing member, being inserted into the fixing hole, one end of the fixing member adjacent to the rope through-hole comprising an end surface, at least part of the end surface abutting against the rope, thereby fixing the rope in the rope through-hole;

wherein the fixing hole comprises a first fixing hole and a second fixing hole, spaced apart from each other and located on the drive shaft;

the first fixing hole and the second fixing hole are disposed on two sides of the rope through-hole, the fixing member comprises a first fixing member and a second fixing member, respectively inserted into the first fixing hole and the second fixing hole, and an end surface of the first fixing member and an end surface of the second fixing member respectively abut against the rope.

2. The rope fixation device according to claim 1, wherein the rope through-hole is a straight line-shaped hole.

3. The rope fixation device according to claim 1, wherein a center line of the rope through-hole intersects an axis of the drive shaft.

4. The rope fixation device according to claim 3, wherein the center line of the rope through-hole is not perpendicular to the axis of the drive shaft.

5. The rope fixation device according to claim 4, wherein center lines of the first fixing hole and the second fixing hole are both perpendicular to the axis of the drive shaft.

6. The rope fixation device according to claim 5, wherein the center lines of the first fixing hole and the second fixing hole are spaced from each other by a first distance; a ratio of the first distance to the length of the rope through-hole is in a range from 0.4 to 0.6.

7. The rope fixation device according to claim 6, wherein the first fixing hole and the second fixing hole are centrally symmetric with respect to the center of the rope through-hole.

8. The rope fixation device according to claim 4, wherein center lines of the first fixing hole and the second fixing hole are both perpendicular to the center line of the rope through-hole.

9. The rope fixation device according to claim 8, wherein the center lines of the first fixing hole and the second fixing hole are spaced from each other by a second distance; a ratio of the second distance to the length of the rope through-hole is in a range from 0.3 to 0.7.

10. The rope fixation device according to claim 9, wherein the first fixing hole and the second fixing hole are centrally symmetric with respect to the center of the rope through-hole.

11. The rope fixation device according to claim 3, wherein the center line of the rope through-hole is perpendicular to the axis of the drive shaft.

12. The rope fixation device according to claim 11, wherein center lines of the first fixing hole and the second fixing hole are both perpendicular to the center line of the rope through-hole, the center line of the first fixing hole is perpendicular to the axis of the drive shaft, and the center line of the second fixing hole is parallel to the axis of the drive shaft.

13. The rope fixation device according to claim 1, wherein at least one of the first fixing hole and the second fixing hole is located on the side wall of the drive shaft.

14. The rope fixation device according to claim 1, wherein the fixing hole is a blind hole, extending in the drive shaft and terminating in the rope through-hole, such that the end surface of the fixing member presses the rope against the inner wall of the rope through-hole.

15. The rope fixation device according to claim 1, wherein the fixing hole comprises a first hole section and a second hole section connected to and in communication with the first hole section; one end of the first hole section is connected to and in communication with the rope through-hole, and the other end of the first hole section is connected to and in communication with the second hole section; a diameter of the first hole section is larger than a diameter of the second hole section;

the fixing member comprises a first segment and a second segment that are connected to each other; the first segment is located in the first hole section, and the second segment is located in the second hole section; an outer diameter of the first segment is larger than an outer diameter of the second segment; the first segment is an elastic member.

16. A rope transmission device for ultrasound probe, comprising a driven shaft and a rope fixation device according to claim 1, wherein the rope of the rope fixation device is connected to the driven shaft.

17. An ultrasound probe, comprising the rope transmission device according to claim 16.

* * * * *